United States Patent [19]

Phillipps et al.

[11] 3,989,686

[45] Nov. 2, 1976

[54] ANAESTHETIC STEROIDS OF THE ANDROSTANE SERIES AND PROCESS FOR PREPARING SAME

[75] Inventors: Gordon Hanley Phillipps, Wembley; David Robert Marshall, Chalfont St. Peter, both of England

[73] Assignee: Glaxo Laboratories Limited, Greenford, England

[22] Filed: Sept. 13, 1974

[21] Appl. No.: 505,763

Related U.S. Application Data

[63] Continuation of Ser. No. 369,141, June 12, 1973, abandoned.

[30] Foreign Application Priority Data

June 15, 1973 United Kingdom............... 28117/73

[52] U.S. Cl..................... 260/239.55 R; 260/397.1; 260/239.5

[51] Int. Cl.$^2$........................................ C07J 21/00
[58] Field of Search................ 260/239.55 R, 397.1

[56] References Cited

UNITED STATES PATENTS 3,856,828   12/1974   Phillipps et al. ................. 260/397.1

*Primary Examiner*—Elbert L. Roberts
*Attorney, Agent, or Firm*—Bacon & Thomas

[57] ABSTRACT

Anaesthetic steroids of the androstane and 19-norandrostane series are described, the steroids possessing a 3α-hydroxy group, a 17α-hydrogen atom and at the 17β-position a —COSH or esterified —COSH group.

7 Claims, No Drawings

ANAESTHETIC STEROIDS OF THE ANDROSTANE SERIES AND PROCESS FOR PREPARING SAME

This is a continuation of application Ser. No. 369,141 filed June 12, 1973 now abandoned.

This invention is concerned with compounds of the and rostane series having anaesthetic activity.

It has long been known that a number of steroids give rise to profound depression of the central nervous system and act pharmacodynamically as anaesthetics or hypnotics. Such compounds have been the subject of considerable study in an attempt to find anaesthetics to replace such substances as thiopentone sodium normally used but well known to be accompanied by some degree of hazard or disadvantage. The literature shows that very many steroid compounds have been studied in this regard. Reviews and discussions of some of the work carried out are to be found, for example, in "Methods in Hormone Research" (Edited by Ralph I. Dorfman, Vol. III Part A, Academic Press, London and New York, 1964, pages 415–475); H. Witzel, Z. Vitamin Hormon-Fermentforsch 1959, 10, 46–74; H. Selye, Endocrinology, 1942, 30, 437–453; S.K. Figdor et al., J. Pharmacol. Exptl. Therap., 1957, 119, 299–309 and Atkinson et al., J. Med. Chem. 1965, 8, 426–432.

A thorough review of the literature indicates that many anaesthetic steroids possess poor activity and/or long induction periods. A variety of undesired side effects such as paraesthesia and vein damage have also been noted.

We have now found anaesthetic activity in a new group of androstane steroids.

Thus the invention provides steroids of the androstane and 19-norandrostane series possessing a $3\alpha$-hydroxy group, a $17\alpha$-hydrogen atom and at the $17\beta$-position, a —COSH or esterified —COSH group, and the salts thereof.

The invention also provides pharmaceutical compositions containing an anaesthetic compound in accordance with the invention and processes for the preparation of the compounds of the invention.

The compounds of the invention may possess substituents at other positions of the steroid nucleus, for example at the 2, $3\beta$ or 11-positions. They may also be unsaturated, for example at the $\Delta^{8(9)}$ and/or $\Delta^1$ or $\Delta^4$ positions. When a hydrogen atom is present at the 5-position it may be in either the $\alpha$ or $\Delta$ configuration, preferably the $\alpha$ configuration.

Compounds having an oxo group at the 11-position are preferred.

In general, the compounds of the invention are good anaesthetics with generally short induction periods, the anaesthetic action at suitable doses being in general instantaneous; these compounds are thus excellent anaesthetics for inducing anaesthesia which is to be maintained e.g. by an inhalation anaesthetic such as ether, halothane, nitrous oxide, or trichloroethylene. The compounds are however capable of maintaining anaesthesia and analgesia to a sufficient degree to enable various surgical operations to be conducted without the aid of an inhalation anaesthetic, the required degree of anaesthesia being maintained if necessary by repeated administration (or even continuous administration). Moreover, the said anaesthetics in accordance with the invention in general give rise to minimal side-effects as compared to many previously described steroidal anaesthetics.

The $17\beta$-substituent is preferably a group of the formula —COSR R is an alphatic, cycloaliphatic, araliphatic, aryl or carbon-attached heterocyclic group.

Examples of aliphatic groups are alkyl, alkenyl and alkynyl groups which may be straight or branched, and unsubstituted or substituted by, for example, one or more N-attached residues of a primary or secondary amine (including secondary heterocyclic amines) or ammonia, halogen atoms (e.g. chlorine), or hydroxy, acyloxy (e.g. $C_{1-6}$ alkanoyloxy such as acetoxy), aryl (e.g. monocyclic aryl such as phenyl), cyano, alkoxycarbonyl (e.g. ethoxycarbonyl), or alkoxy (which may itself be substituted by an N-attached residue of a primary or secondary amine or ammonia as referred to above) groups.

Cycloaliphatic groups may for example be cycloalkyl groups or substituted cycloalkyl groups, e.g. cyclohexyl groups.

Aryl groups may for example be monocyclic aryl groups such as phenyl groups, which may for example be substituted by alkyl, alkoxy, alkoxycarbonyl, alkylthio, hydroxy or nitro groups or halogen (e.g. iodine) atoms.

Araliphatic groups may for example be aralkyl, aralkenyl or aralkynyl groups in which the aryl portions may be as just described.

Carbon-attached heterocyclic groups may be saturated or unsaturated, substituted or unsubstituted, monocyclic or bicyclic, and may contain one or more hetero atoms such as nitrogen, oxygen or sulphur.

The primary or secondary amines referred to above may for example be monoalkyl- or dialkylamines, which may be substituted, for example, by hydroxy, oxo, alkoxy, or acyloxy (e.g. $C_{1-6}$ alkanoyloxy) groups, or halogen atoms. Alternatively, the amines may for example be monoaryl- or monoaralkylamines or diaralkyl- or diarylamines, the aryl portions conveniently being monocyclic (e.g. phenyl) and either unsubstituted or substituted, for example, by halogen atoms or alkoxy or hydroxyl groups. Again, the amines may be heterocyclic amines, which are preferably monocyclic and may contain a further hetero atom such as nitrogen, oxygen and sulphur. The heterocyclic amines may be saturated or unsaturated, and unsubstituted or substituted, for example by one or more alkyl, aryl (e.g. monocyclic aryl such as phenyl), aralkyl (e.g. benzyl), hydroxy, oxo, alkoxy, alkoxycarbonyl or acyloxy (e.g. $C_{1-6}$ alkanoyloxy) groups.

The N-attached residues may be conveniently defined as having the formula —NR$^1$R$^2$ where R$^1$ and R$^2$ which may be the same or different, are hydrogen atoms or alkyl, aryl or aralkyl groups (which may be substituted as just indicated), or, when taken together with the nitrogen atom, represent a heterocyclic ring which may contain a further hereto atom and may be saturated, unsaturated, unsubstituted or substituted as just indicated. A preferred group is morpholino.

In all the cases referred to above, the alkyl, alkenyl and alkynyl groups, and the corresponding portions of araliphatic groups, and the alkoxy groups generally have 1–10, preferably 1–6, carbon atoms. Heterocyclic groups may generally have 5 to 10, e.g. 5 or 6, ring members.

R is preferably an unsubstituted $C_{1-6}$ alkyl group, such as methyl or ethyl group, or such a group substituted by an N-attached residue as described above, particularly a morpholino or thiamorpholino group.

Examples of various substituents which may be present at other positions of the steriod nucleus will now be described. As indicated above, it is generally preferred that an oxo group should be present at the 11-position. It is also preferred that when a 5β-hydrogen atom is present at 2β-substituent should be absent.

Examples of substituents which may be present at the 2β-position include an acyloxy group having for example 1 to 9 carbon atoms, an ether or thioether group (i.e. the residue of an alcohol, a phenol or a thiol) containing for example 1-9 carbon atoms (e.g. methoxy), an alkyl or cycloalkyl group for example containing up to 9 carbon atoms, an aryl group (e.g. a phenyl group), an aralkyl group (e.g. a benzyl group), a hydroxy group, a thiocyanato group, a nitro-oxy group, or a halogen atom.

Acyloxy substituents (which may be saturated or unsaturated) include lower ($C_1-C_6$) alkanoyloxy groups, (substituted if desired, for example, with one or more halogen, e.g. chlorine atoms, lower alkoxy, amino or substituted amino groups), aroyloxy groups (e.g. a benzoyloxy group), or aralkanolyloxy groups (i.e. a phenylacetoxy group).

Ether substituents, which may be saturated or unsaturated, include lower ($C_1-C_6$) alkoxy groups, lower alkenyloxy groups (e.g. an allyloxy group), cycloalkoxy groups (e.g. a cyclohexyloxy group), arloxy groups (e.g. a phenoxy group) and aralkoxy groups (e.g. a benzyloxy group). Thioether groups corresponding to the above-mentioned ether groups are representative of 2β-thioether substituents.

The 2β-substituent may alternatively be an azido, sulphonyloxy (e.g. tosyloxy) group of an acylthio group.

Examples of 2β-alkyl groups include especially lower alkyl groups containing 1–5 carbon atoms such as methyl, ethyl, propyl butyl, isobutyl and t-butyl groups. An example of a cycloalkyl group is a cyclohexyl group.

Examples of lower alkanolyoxy 2β-substituents include acetoxy, propionyloxy, butyryloxy piperidinoacetoxy, morpholinoacetoxy, diethylaminoacetoxy and chloroacetoxy groups. Examples of lower alkoxy groups include methoxy, ethoxy, propoxy, isopropoxy, n-butoxy and t-butoxy groups, and the corresponding thio compounds exemplify lower alkyl thio substituents.

Lower alkoxy and lower alkylthio substituents at the 2β-position may themselves be substituted for example by one or more halogen (e.g. chlorine) atoms, lower alkoxy, esterified carboxyl (e.g. ethoxycarbonyl), hydroxy, amino or substituted amino (e.g. morpholino) groups, or substituted or unsubstituted acyloxy (e.g. morpholinoacetoxy, chloroacetoxy or diethylaminoacetoxy), or heterocyclic groups, e.g. a tetrahydrofuranyl group. Alkyl, cycloalkyl and aryl groups may also be substituted.

The 2β-position may also carry amino substituents, e.g. amino or substituted amino groups, for example mono- or di-alkylamino or saturated, unsaturated or aromatic heterocyclic amino groups, e.g. a morpholino group.

Particularly important 2β-substituents are methyl, ethoxy and methoxy groups.

Examples of substituents which may be present at the 2α-position are alkyl groups, e.g. having 1 to 6 carbon atoms such as methyl or ethyl, or halogen atoms, e.g. chlorine or bromine.

Examples of substituents which may be present at the 3β-position are alkyl groups, e.g. having 1 to 6 carbon atoms such as methyl, ethyl or pentyl.

An oxo group may be present at the 11-position and compounds having this substituent are particularly important. Alternatively, a hydroxy group may be present at the 11-position, in either the α configuration or, in the presence of absence of an α-alkyl or alkenyl ($C_{1-6}$) group (e.g. methyl or allyl), in the β configuration. Another possible grouping is an epoxy group linked also to the 9-position.

Certain of the compounds of the invention, e.g. those containing a basic nitrogen atom, are capable of forming acid addition salts and this has the advantage of tending to improve the water solubility of the compounds. Such salts include, in the case of amino-substituted compounds, hydrochlorides, hydrobromides, phosphates, sulphates, p-toluenesulphonates, methanesulphonates, citrates, tartrates, acetates, ascorbates, lactates, maleates and succinates.

When these salts are used as anaesthetics they should be non-toxic, i.e. physiologically acceptable in the dosage at which they are administered. Other salts may, however, be of use in, for example, isolation of the product from a synthetic reaction.

Particularly preferred compounds in accordance with the invention by virtue of their excellent anaesthetic properties are:

1. 3α-Hydroxy-17β-methylthiocarbonyl-5α-androstan-11-one;
2. 3α-Hydroxy-17β(2'-morpholinoethylthiocarbonyl)-5α-androstan-11-one; and its salts.

PHARMACEUTICAL FORMULATIONS

The anaesthetic compounds of the invention may be formulated as convenient, following generally known pharmaceutical practices, (including both human and veterinary medical practices), with the aid of one or more pharmaceutical carriers or excipients. For anaesthetic purposes, the steroids will be given by injection and thus one aspect of this invention comprises an anaesthetic composition for parenteral administration comprising an anaesthetic compound in accordance with the invention in a parenterally acceptable vehicle.

When the anaesthetic compounds are sufficiently soluble in water (e.g. the salts, particularly those referred to above) they may be formulated in aqueous solutions (e.g. isotonic sterile solutions) or supplied as e.g. powders for dissolution in a sterile medium before use. Many of the anaesthetic steroids of the invention are poorly soluble in water. We have found however that they may be formulated for parenteral administration in an aqueous solution of a parenterally acceptable non-ionic surface active agent. These surface active agents may also be used even where the steroid is sufficiently water soluble as they may reduce the risk of thrombophlebitis.

The compounds of the invention may thus be formulated as solutions or suspensions in aqueous media, such suspensions being generally described for example in U.S. patent application Ser. No. 208,922, filed Dec. 16, 1971 and now Pat. No. 3,816,624.

The non-ionic surface active agents used for the purpose of this invention are generally those of the water-soluble type, conveniently having an HLB value of at least 9, preferably at least about 12, advantageously at least about 13. Preferably the HLB value of the surface active agent is not greater than about 18. A mixture of surface agents may be used, in which case it is the HLB value of the mixture which is conveniently between the values just mentioned.

The surface active agent must naturally be one which is physiologically compatible, i.e. of itself give rise to no physiologically unacceptable side effects in the dosages employed in the intended species to be treated (man or animal).

Surface active agents for use in accordance with the invention are for example to be found among the following non-ionic surfactants and classes of surfactants:

Polyoxyethylated derivatives of fatty (C12–C20) glyceride oils, e.g. castor oil, containing from 35 to 60 oxyethylene groups per mole of fatty oil. Polyoxythylene ethers (containing from 10 to 30 oxyethylene groups) of long chain alcohols (containing for example from 12–18 carbon atoms).

Polyoxyethylene-polyoxypropylene ethers containing from 5 to 150 and from 15 to 50 oxyethylene and oxypropylene groups respectively. Polyoxyethylene ethers (containing from 6 to 12 oxyethylene groups) of alkyl phenols the alkyl groups of which preferably contain 6–10 carbon atoms.

Polyoxyethylated (containing from 15 to 30 oxyethylene groups) fatty acid (e.g. C12–18) esters of sugar alcohol anhydrides e.g. sorbitan or mannitan.

Long-chain (e.g. C10–16) alkanoyl mono- and di-alkanolamides (the alkanol portions of which for example contain 1–5 carbon atoms) for example lauroyl mono- and di-ethanolamides. Polyethylene glycol esters (containing from 6 to 40 ethylene oxide units) of long chain fatty acids (containing for example 12–18 carbon atoms) e.g. polyethyleneglycol monooleate (containing for example 8 ethylene oxide units).

Other useful surfactants include phospholipids such as lecithins, e.g. egg or soyabean lecithins.

Examples of non-ionic surface active agents, of the foregoing types, useful in accordance with the invention include:

Cremophor EL, a polyoxyethylated castor oil containing about 40 ethylene oxide units per triglyceride unit;

Tween 80, polyoxyethylene sorbitan monooleate containing about 20 ethylene oxide units;

Tween 60, polyoxyethylene sorbitan monstearate containing about 20 ethylene oxide units; and Tween 40, polyoxyethylene sorbitan monopalmitate containing about 20 ethylene oxide units.

The proportion of surface active agent to be used in the compositions of this invention depends upon its nature and upon the concentration of steroid desired in the final composition.

In preferred compositions according to the invention the proportion of surfactant is preferably at least 5% by weight and advantageously above 10% by weight. A very convenient proportion of surfactant has been found to be 20% by weight but 30% and up to 50% may be used. The proportions of surfactant are expressed by weight in relation to the total volume of the composition.

In all cases simple tests enable one to determine the relative proportions of surface active agent required.

As will be clear, the proportion of steroid which is dissolved in the aqueous medium according to the invention depends upon the water-solubility of the steroid and, where present, the nature and amount of surface active agent used. The composition will generally contain at least 1 mg/ml of steroid but solutions can be made containing for example up to 10 mg/ml of steroid or even 300 mg/ml. The more concentrated solutions can usually only be made with the water-soluble steroids.

The anaesthetic compositions according to the invention are generally administered by intravenous injection although as is known in the anaesthetic art in certain cases, e.g. with young children, intramuscular injection might be preferred.

As is usual in the case of anaesthetics, the quantity of steroid used to induce anaesthesia depends upon the weight of the individual to be anaesthetised. For intravenous administration in the average man a dose of from 0.2 to 20 mg/kg will in general be found to be satisfactory to induce anaesthesia, the preferred dose being within the range of from 0.5 to 5 mg/kg. The dose will naturally vary to some extent dependent upon the physical condition of the patient, and the degree and period of anaesthesia required, all as is well known in the art. It is thus possible by adjustment of the dose to achieve durations of anaesthesia varying from about 10 minutes to up to an hour or more. If it is desired to maintain prolonged anaesthesia, repeated doses of the compositions of this invention may be used, such repeated doses being generally either of the same order or lower than the original dose. Alternatively continuous administration may be undertaken at for example a rate of 0.025–2.0, e.g. 0.09–1.8, mg/kg/Min.

Where the anaesthetic compositions are administered intramuscularly, higher doeses are generally necessary.

COMPOUND PREPARATION

The compounds of the invention may be prepared by any convenient method and in most cases they can be prepared by conventional techniques. They may for example be prepared by reacting a corresponding compound having a $17\beta$-carboxylic acid group, or a reactive derivative thereof, with a compound of the formula RSH.

Compounds having a $17\beta$-COSH group may for example be prepared by reacting the corresponding $17\beta$-COCl compound with hydrogen sulphide.

The esters of the invention are most conveniently prepared by reacting a reactive derivative of a compound having a $17\beta$-carboxylic acid group with a compound of the formula RSH. The reactive derivative may be an acid halide, anhydride or ester (e.g. a $C_{1-6}$ alkyl ester), $17\beta$-carbonyl chlorides being preferred.

The thioesterification reaction is conveniently carried out in the presence of an inert organic solvent, for example, a halogenated hydrocarbon e.g. methylene chloride or chloroform, an aromatic hydrocarbon, e.g. benzene or an ether e.g. diethyl ether or tetrahydrofuran.

In general, the thioesterification reaction may be effected in the presence of an acid binding agent, for example, a tertiary organic base such as pyridine or triethylamine or an inorganic base such as an alkali metal carbonate or bicarbonate e.g. sodium carbonate or bicarbonate. However, when a thiol reacted with the acid halide itself contains a basic substituent, for example an amino or substituted amino group, e.g. 2-morpholinoethane thiol, the basic substitutent may itself act as the acid binding agent.

The reaction of a carboxylic acid halide with the compound RSH may for example be effected at temperatures between $-20°$ C to $+110°$ C.

The acid halides used in the above reaction may be prepared by conventional methods, for example, from the corresponding 17β-carboxylic acid by reaction with a suitable halogenating agent e.g. a thionyl, phosphoryl or oxalyl halide. When it is desired to use the acid chloride for the preparation of the esters according to the invention, thionyl chloride, phosphoryl chloride or oxalyl chloride are preferably used. The 17β-carboxylic acids may be prepared by oxidation of the 17β-acetyl group of a corresponding pregnane. This oxidation may for example be effected in solution using a hypohalite salt e.g. an alkali metal or alkaline earth metal hypohalite as oxidising agent. Suitable hypohalites include, for example, sodium and potassium hypochlorites, hypobromites and hypoiodites.

The oxidation process is conveniently carried out in aqueous or non-aqueous media. Thus the reaction may for example be effected in an aqueous water-miscible organic solvent for example a water-miscible ether e.g. dioxan, tetrahydrofuran, diglyme and 1,2-dimethoxyethane or a water-miscible alcohol e.g. t-butanol. Aqueous dioxan is the preferred solvent.

The oxidation may be effected at a temperature of from −20° to 100° C, a temperature of from 5° to 10° C being preferred.

The 17β-thioesterified compounds according to the invention may also be prepared, for example, by reacting the corresponding 17β-carboxylic acid with a compound RSH in the presences of a catalyst.

Acid catalysts have generally been found to be convenient e.g. sulphuric, hydrochloric, perchloric or p-toluene sulphonic acid. In some circumstances the RSH compound can be used as the reaction solvent, which may conveniently contain dry hydrogen chloride as catalyst. The reaction is advantageously effected at an elevated temperature, for example under reflux.

Compounds having an esterified 17β-COSH group may also be prepared from the corresponding thiol acids by esterification e.g. by reacting an alkali metal salt of the thiol acid with an alkyl halide or equivalent reagent.

Compounds according to the invention possessing a 17β-alkylthiocarbonyl group substituted by an amino group may be prepared by first reacting the corresponding 17β-carboxylic acid or reactive derivative thereof with a thiol possessing a readily eliminatable substituent (e.g. a halogen atom such as chlorine or bromine). The ester produced (which may of course be prepared by other routes) carries the readily eliminatable substituent in the ester group. The product is then reacted with ammonia or an amine (e.g. of the formula $HNR^1R^2$ such as morpholine and thiamorpholine).

17β-(2'-Chloroalkylthiocarbonyl intermediates required for this reaction may also be prepared by reacting a 17β-chlorocarbonyl compound (in which the 3α-hydroxy group is protected, e.g. as a nitro-oxy group) with a thiirane, e.g. thiirane or a thiirane containing one or more alkyl substituents (e.g. having 3–10, preferably 3–6 carbon atoms). The reaction may be performed in a solvent such as ether, e.g. at reflux, and may for example be used to prepared 17β-(2'-chloroethylthiocarbonyl) compounds.

The 3α-oxygenated 5α-androstane anaesthetics according to the invention may also, for example, be prepared from the corresponding 3β-hydrocarbonsulphonyloxy-5α-androstane in a manner analogous to that described by Nagata et al. (Helv. Chim, Acta, 1959, 42, 1399) by reaction with a carboxylic acid or a salt thereof whereby a 3α-acyloxy-5α-androstane is formed. The 3α-hydroxy steroid may then be obtained by basic hydrolysis.

In the preparation of compounds in accordance with the invention possessing an optional substituent or a carbon-carbon double bond such as described above, it is convenient for this substituent or unsaturation to be present in the starting material. Alternatively, these substituents or unsaturation may be introduced subsequently, for example by generally known techniques using known compounds as starting materials. For convenience a number of suitable methods are set out below.

Substitution at the 2β-position in the 5α-series can be effected for example by way of the corresponding 2α,3α-epoxy compound. The epoxy compound itself may be prepared by first dehydrating a 3-hydroxy compound to give the corresponding $\Delta^2$ compound (e.g. by first tosylating the hydroxy group and then detosylating the product), and then treating the $\Delta^2$ compound with a peracid to form the 2α, 3α epoxide ring.

A 2β-substituent may then be introduced by the method described in U.S. patent application Ser. No. 197,915, filed Nov. 11, 1971 and indicated as being in condition for allowance on Aug. 19, 1974. This general method may be used to introduce all the 2β-substituents described above.

Methods for introducing substituents at the 2α, 3β, and 11-positions are described in U.S. pat. application Ser. No. 208,959, filed Dec. 16, 1971 and now abandoned in favor of a pending continuation thereof Ser. No. 443,451, filed Feb. 19, 1974. These or analogous methods may be used to introduce all the substituents referred to above at these positions. For example, an 11-alkenyl group may be introduced by methods analogous to those described in U.S. patent application Ser. No. 208,959 for the introduction of an 11-alkyl substituent.

5α-Steroids possessing $\Delta^1$ unsaturation may also be prepared by known methods, but we prefer to use a method which comprises dehydrobrominating a 2β-bromo-3α-hydroxy steroid, if desired protecting the 3α-hydroxy group (e.g. as its tetrahydropyranyl ether), to give the $\Delta^1$ compound, and then deprotecting the product where necessary to give the desired 1,2-dehydro-3α-hydroxy-compound.

The dehydrobromination may be effected, for example using a nitrogen containing Lewis base such as a di-lower alkyl lower acylamide e.g. dimethylformamide or dimethylacetamide advantageously in the presence of an alkali metal or alkaline earth metal carbonate, for example calcium carbonate.

In general it has been found convenient to effect the dehydrobromination at an elevated temperature for example from 80° to 170° C. Lower temperatures may be employed when a lithium or calcium halide is present.

Compounds possessing $\Delta^4$ unsaturation may be prepared from $\Delta^3$-steroids by methods analogous to these described for obtaining the $\Delta^1$ compounds from $\Delta^2$ steroids. Alternatively, $\Delta^4$-steroids may be obtained by the methods described in U.S. patent application Ser. No. 194,918, filed Nov. 2, 1971 and now U.S. Pat. No. 3,825,565.

Compounds having a double bond between the 8 and 9-positions and an 11-oxo group may be prepared for example by the method described in U.S. pat. application Ser. No. 208,959. These compounds may also be prepared by dehydration of the corresponding 9α-hydroxy compound, for example using thionyl chloride in pyridine.

5α-Steroids of the invention may also be prepared from the corresponding 3-oxo compounds by stereospecific reduction, e.g. by the method of Browne and Kirk (J. Chem. Soc. C, 1969, 1653) or by the method of U.S. patent application Ser. No. 305,246, filed Nov. 10, 1972 and now U.S. Pat. No. 3,822,298. The latter method preferably uses a pre-formed iridium catalyst reduction system. For example, a reduction system may be prepared from an iridium acid or salt (e.g. chloroiridic acid), a trivalent phosphorus compound such as a phosphorous acid ester (e.g. trimethyl phosphite), water and an organic reaction medium (e.g. an alcohol such as isopropanol). The reduction system is then neutralised (e.g. to a pH of 6 to 8.5) with an organic base such as a secondary or tertiary amine (e.g. triethylamine) and reacted with the steroid. When the catalyst system is preformed by heating at reflux for 16 to 72 hours, the reduction can be accomplished in 2–3 hours at reflux; longer times may be necessary at room temperature.

5β-Steroids may similarly be prepared by hydride reduction of 3-oxo steroids.

In various of the transformations herein described, as will be clear to these skilled in the art, it may be necessary to protect a 3α-hydroxy group if such is present. Thus, for example, it may be necessary in oxidation reactions and during conversions of a 17β-carboxylate group to an acid halide group. Such temporary protection may be effected in known manner, e.g. by formation of a 3α-ester group which may be readily re-converted to a free hydroxy group. Lower alkanoyl groups are frequently very satisfactory and may be removed by hydrolysis. For many purposes we have found that temporary protection of the 3α-hydroxy group by formation of a nitrate ester thereof is especially convenient. 3α-Nitro-oxy groups may be readily converted to 3α-hydroxy groups by catalytic hydrogenation or by chemical reduction with for example a metal/acid system, such as zinc and acetic acid. The 3α-hydroxy group may also be protected in the form of an ether, e.g. a tetrahydropyranyl ether.

The following Examples are given by way of illustration only. All temperatures are in degrees Celsius. The term petrol as used herein refers to petroleum ether (b.p. 60°–80°).

Rotations were determined in chloroform at about 1% W/V concentration unless otherwise stated. Preparative thin layer chromatography (t.l.c.) was carried out on silica gel.

EXAMPLE 1

3α-Hydroxy-17β-methylthiocarbonyl-5α-androstan-11-one

Zinc dust (750 mg.) was added to a stirred solution of 17β-methylthiocarbonyl-3α-nitro-oxy-5α-androstan-11-one (439 mg) in glacial acetic acid (10 ml) at room temperature. After 15 min. the reaction mixture was diluted with chloroform, filtered, washed with water, aqueous 10% sodium bicarbonate and water. The residue remaining after removal of the solvent was purified by t.l.c. to afford the title compound (288 mg) as a white solid; $[\alpha]_D + 78°$ (c 0.5).

EXAMPLE 2

3α-Hydroxy-17β(2'-morpholinoethylthiocarbonyl)-5α-androstan-11-one

Zinc dust (2.5 g.) was added to a stirred solution of 17β(2'-morpholinoethylthiocarbonyl)-3α-nitro-oxy-5α-androstan-11-one (1.034 g) in glacial acetic acid at room temperature. After 10 min. the reaction mixture was diluted with chloroform, filtered, washed with water, aqueous 10% sodium bicarbonate and water. Removal of the solvent afforded a residue which on addition of a little ether rapidly crystallised. Filtration afforded the title compound (718 mg);$[\alpha]_D + 73°$, (c 0.8).

EXAMPLE 3

3α-Hydroxy-17β(2'-morpholinoethylthiocarbonyl)-5α-androstan-11-one salts (Dihydrogen citrate, dihydrogen phosphate).

Aqueous $^M/10$ citric acid (phosphoric acid) (1 equivalent) was added to a solution of 3α-hydroxy 17β(2'-morpholinoethylthiocarbonyl)-5α-androstan-11-one (80) in ethanol. This solution was evaporated to dryness, water added and the mixture filtered. The filtrate was diluted with water to give solutions of the title compounds at a concentration of 10 mg/ml. with respect to steroid free base taking into account the material removed by filtration.

EXAMPLE 4

3α-Hydroxy-17β-methythiocarbonyl-5β-androstane

A solution of 3α-nitro-oxy-5β-androstane-17β-carboxylic acid (lg) in benzene (80ml) and oxalyl chloride (3ml) was refluxed for 3 hours and evaporated to a foam (1.1 g).

The foam was dissolved in dry ether (50 ml) and pyridine (5 ml). Methanethiol (2 ml) was added and the mixture was left at room temperature overnight. Evaporation of the solvents left a residue which was partitioned between chloroform and water. The organic layer was washed with water, dried ($Na_2SO_4$) and evaporated to a solid (700 mg).

The solid (700 mg) was dissolved in acetic acid (50 ml) and the solution was stirred with zinc powder (2.8 g) for 1 hour. The mixture was filtered, the filtrate was evaporated to low bulk, and the residue was partitioned between chloroform and 10% aqueous sodium hydrogen carbonate. The organic layer was washed with aqueous sodium hydrogen carbonate and water, dried ($Na_2SO_4$), and evaporated to leave a solid which was purified by chromatography on silica in chloroform to give the title compound; m.p. 157°–8°, $[\alpha]_D+91.5°$.

EXAMPLE 5 2β-Ethoxy-17

β-ethylthiocarbonyl-3α-hydroxy-5α-androstan-11-one

A mixture of 2β-ethoxy-3α-nitro-oxy-5α-androstan-11-one 17β-carboxylic acid (3 g), oxalyl chloride (7 ml) and dry benzene (250 ml) was refluxed for 4 hours. Evaporation of the reaction mixture gave the crude acid chloride (3.2 g) which was dissolved in dry ether (100 ml) and treated with ethanethiol (1.5 ml) in the presence of anhydrous pyridine (3 ml). After 18 hours at room temperature, the reaction mixture was evaporated to an oil by passing air through it. The residual oil was dissolved in ether and the solution was washed with water, dried ($MgSO_4$), and evaporated to give crude 2β-ethoxy-17β-ethyl-thiocarbonyl-3α-nitro-oxy-5α-androstan-11-one (2.9g). This was treated with zinc dust (2.5 g) and acetic acid (35 ml) for 20 minutes before addition of chloroform (200 ml) and filtering. The organic phase was washed successively with water, aqueous sodium hydrogen carbonate and water before drying (MgSO$_4$) and evaporating to an oil (1.8 g). This oil was purified by preparative t.l.c. (CHCl$_3$) and trituration with ether to give the title compound as crystals, m.p. 186°–189°, [α]$_D$ +66°.

EXAMPLE 6
17β-(2'-Chloroethylthiocarbonyl)-3α-hydroxy-5α-androstan-11-one

A solution of 17β-(2'-chloroethylthiocarbonyl)-3α-nitro-oxy-5α-androstan-11-one (160 mg) in acetic acid (2.8 ml) was stirred for 1 hour at room temperature with zinc dust (0.57 g). The reaction mixture was diluted with chloroform (4 ml), neutralized to ca pH7 with aqueous sodium carbonate, filtered and the organic phase was separated, washed with water, dried (MgSO$_4$) and evaporated in vacuo. The residue was subjected to preparative t.l.c. in chloroform to give the title compound as a foam (107 mg), [α]$_D$ +68°(c, 0.1),

EXAMPLE 7
3α-Hydroxy-17β-(2'morpholinoethylthiocarbonyl)-5α-androstan-11-one A mixture of 17β-(2'-chloroethylthiocarbonyl)-3α-hydroxy-5α-androstan-11-one (50 ml), morpholine (0.5 ml) and dry tetrahydrofuran (1 ml) was refluxed for 50 hours. The reaction mixture was diluted with chloroform and washed successively with aqueous sodium hydrogen carbonate and water before drying (Na$_2$SO$_4$) and evaporating to an oil (48 mg). The oil was subjected to preparative t.l.c. (CHCl$_3$) to give a mixture (30 mg) in which the title compound predominated, as judged by thin layer chromatography on silica in ethanol-chloroform (1:19) (R$_F$ 0.2) and its proton magnetic resonance spectrum, τ (in CDCl$_3$) 9,39,9.00 and comparison with the product of Example 2.

EXAMPLE 8
0.025g of 3α-hydroxy-17β(methylthio)carbonyl-5α-androstan-11-one were added to 2 ml. of acetone at 20°C. The resulting mixture was added to 2 g. of Cremophor EL at 20°C and was then ground with a tissue grinder. The acetone was removed by a vigorous stream of nitrogen. The suspension was diluted with sterile distilled water containing 0.05 g of sodium chloride to give a final volume of 10 ml.

PREPARATION 1
17β(2'-morpholinoethylthiocarbonyl)-3α-nitro-oxy-5α-androstan-11-one Morpholinoethanethiol (1.2 ml) was added to a stirred solution of 17β-chlorocarbonyl-3α-nitro-oxy-5α-androstan-11-one (1.58 g) in dry ether (50 ml) at room temperature. After ca. 40 hr. at 0° the reaction mixture was diluted with ether and washed with aqueous 10% sodium bicarbonate and water. Removal of the solvent afforded the title compound as a white solid (1.639 g); [α]$_D$ +83°, (c 0.6).

PREPARATION 2
17β-Methylthiocarbonyl-3α-nitro-oxy-5α-androstan-11-one

Methanethiol was bubbled into a dry ethereal solution of 17β-chlorocarbonyl-3α-nitro-oxy-5α-androstan-11-one(1.45 g) for 45 min. The reaction mixture was diluted with chloroform (50 ml.), washed with water, dried (MgSO$_4$), filtered and evaporated to a residue which, after purification by t.l.c. afforded the title compound (574 mg); [α]$_D$ +90°, (c0.6).

PREPARATION 3
17β-Chlorocarbonyl-3α-nitro-oxy-5α-androstan-11-one

3α-Nitro-oxy-11-oxo-5α-androstane-17β-carboxylic acid (500 mg.) and oxalyl chloride (2 ml.) were refluxed with dry benzene (50 ml.). After 5 hours the solvents were removed under reduced pressure and the resultant froth was triturated with dry ether (70 ml.). The solution was filtered, evaporated and dried in vacuo to give title compound (353 mg.) ν$_{max}$. 1780, 1705 and 1620 cm.$^{-1}$ in bromoform.

PREPARATION 4
3α-Nitro-oxy-11-oxo-5α-androstane-17β-carboxylic acid

Fuming nitric acid (13 ml.) was added slowly with stirring to acetic anhydride (40 ml.) between −5° and 0°. This nitrating mixture was stirred with a solution of 3α-hydroxy-11-oxo-5α-androstane-17β-carboxylic acid (8 g.) in chloroform (240 ml.) for 1 hour, between −5° and 0°. The mixture was poured into 2N-sodium hydroxide solution and stirred for 30 minutes. The mixture was extracted with chloroform and the combined extracts were washed with water and evaporated to a residue. The residue was stirred for 1 hour with ethanol (50 ml.), ether (250 ml.) and water (500 ml.), the pH being adjusted to 10–11 with sodium hydroxide. The aqueous layer was acidified with hydrochloric acid and extracted with chloroform. The extract was washed with water, dried (Na$_2$SO$_4$) and evaporated to a residue. Crystallisation from chloroform and benzene gave title compound (4.707 g.) as colourless rods, m.p. 214°–218° (dec.), [α]$_D$ −73°.

PREPARATION 5
3α-Hydroxy-11-oxo-5α-androstane-17α-carboxylic acid

A solution of sodium hydroxide (2.1 g.) in water (18 ml.) was stirred at −5° and bromine (0.75 ml.) was added slowly, the temperature being maintained between −5° and 0°. Cold dioxan (12 ml.) was added. This sodium hypobromite solution was stirred at 0° until required.

3α-Hydroxy-5α-pregnane-11,20-dione (1.4 g.) was dissolved in dioxan (55 ml.) and water (16 ml.) and stirred at 5°. The sodium hypobromite solution was added and the mixture stirred for 3 hours between 5° and 10°.

Sodium sulphite heptahydrate (800 mg.) in water (5 ml.) was added and the mixture refluxed for 15 minutes.

The mixture was acidified hot with concentrated hydrochloric acid, filtered, evaporated until crystals appeared and extracted into chloroform. The extract was washed with water, dried and evaporated to a residue which was crystallised from benzene, chloroform and petrol to give title compound (660 mg.) as colourless needles; m.p. 265°–270°

PREPARATION 6

17β-2'-Chloroethylthiocarbonly)-3α-nitro-oxy-5α-androstan-11-one

A solution of 17α-chlorocarbonyl3α-nitro-oxy-5α-androstan-11-one (1 g) in dry ether (15 ml) and thiirane(0.8 ml) was heated under reflux for 20 hours. The solvent and thiirane were removed in vacuo and the residue was subjected to preparative t.l.c. 41 (CHCl$_3$) to give the title compound (190 mg);[α]$_D$–86° (c, 0.8).

PREPARATION 7

3α-Nitro-oxy-5β-androstane-17β-carboxylic acid

Fuming nitric acid (13 ml.) was added with stirring to acetic anhydride (40 ml.) keeping the temperature between −10° and 0°. A suspension of 3α-hydroxy-5α-androstane 17β-carboxylic acid (8.0 g.) in chloroform (300 ml.) was added to the nitrating solution, keeping the reaction temperature at ca. 0°. The reaction mixture was stirred to ca. 0° for 1.5 hours and then poured into aqueous sodium hydroxide (290 ml. 2N). This, after stirring (20 minutes), was separated and the aqueous phase further extracted with chloroform (100 ml.). The residue, following evaporation, was dissolved in ethanol (50 ml.), water (500 ml.) and ether (250 ml.) and the whole solution brought to ca. pH10 with aqueous sodium hydroxide (2N). After separation, the aqueous phase was stirred and acidified with aqueous hydrochloric acid (2N) whereupon the product precipitated as a white solid. This was filtered, washed with water, and dried to afford title compound (8.5 g.) as a white solid; m.p. 221–223°. A sample was recrystallised from chloroform/petrol; white flakes, m.p. 222°–225°λ dec.; [α]$_D$ −75°, (c 0.4%).

Similar methods to those described in the above Examples and Preparations may be used to prepare:

3α-hydroxy-2β-methyl-17β-2'-morpholinoethylthiocarbonyl)-5α-androstan-11-one;

3α-hydroxy-2β-methoxy-17β-(2'-morpholinoethylthiocarabonyl)-5α-androstan-11-one;

2β-chloro-3α-hydroxy-17β-(2'-morpholinoethylthiocarbonyl)-5α-androstan-11-one;

3α-hydroxy-17β-(2'-morpholinoethylthiocarbonyl)-5α-androstran-11-one hydrochloride, tartrate, mesylate and ascorbate;

3α-hydroxy-17β-(2'-thiamorpholinoethylthiocarbonyl)-5α-androstan-11-one;

3α-hydroxy-17β-(2'-morpholinoethylthiocarbonyl)-5α-androstan-1-en-11-one;

3α-hydroxY-17β-(4'-morpholinobutylthiocarbonyl)-5α-androstan-11-one;

'α-hydroxy-17β-(2'-chloroethylthiocarbonyl-5α-androstran-11-one;

3α-hydroxy-17β-(2'-methylmorpholinoethylthiocarabonyl)-5α-androstan-11-one.

We claim:
1. A steriod of the formula:

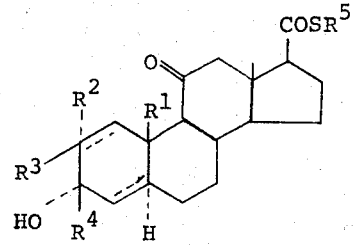

where R$^1$ is hydrogen or methyl; R$^2$ is hydrogen or methyl; R$^3$ is hydrogen or when R$^2$ is hydrogen, C$_{1-6}$ alkoxy, C$_{1-5}$ alkyl, thiocyanato or halogen, R$^4$ is hydrogen or methyl; R$^5$ is C$_{1-6}$ alkyl or C$_{1-6}$ alkyl substituted by halogen or substituted by a group —NR$^6$R$^7$ where R$^6$ and R$^7$ are the same or different C$_{1-6}$ alkyl groups or R$^6$ and R$^7$ taken together with the nitrogen atom to which they are attached form a group selected from the group consisting of morpholino, morpholino substituted with C$_{1-6}$ alkyl, and thiamorpholino and the dotted lines represent a double bond at either one of these positions, providing that R$^2$ and R$^3$ together represent hydrogen when there is a double bond at the 1,2-position.

2. A steriod according to claim 1, which is of the androstane series and contains a 5 -hydrogen atom.

3. A steroid according to claim 1 which contains a basic nitrogen atom, said steroid being in the form of its hydrochloride, hydrobromide, phosphate, sulphate, p-toluenesulphonate, methanesulphonate, citrate, tartrate, acetate, ascorbate, lactate, maleate or succinate.

4. A steroid according to claim 1 which is 3α-hydroxy-17β-methylthiocarbonly-5α-androstan-11-one; or 3α-hydroxy-17β-(2'morpholinoethyl-thiocarbonyl)-5αandrostan-11-one, and their physiologically acceptable salts.

5. A process for the preparation of a compound as claimed in claim 1 which comprises:
   a. reacting a 17β-halocarbonyl androstane having a protected 3α-hydroxy group with a thiirane to form the corresponding 17β-(2'haloalkylthiocarbonyl) compound;
   b. reacting the (a) compound with ammonia, a primary or secondary amine to form a 17β-aminoalkythiocarbonyl compound; and
   c. regenerating the 3α-hydroxy group from its protected form.

6. A steroid according to claim 1 wherein R$^3$ is a C$_{1-6}$ alkoxy group.

7. A steroid according to claim 1 wherein R$^5$ is C$_{1-6}$ alkyl substituted by a morpholino group attached through the morpholino nitrogen.

* * * * *